(12) United States Patent
Quinn

(10) Patent No.: US 6,540,714 B1
(45) Date of Patent: Apr. 1, 2003

(54) BLOOD VESSEL CATHETER

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 0 days.

(21) Appl. No.: 09/651,455

(22) Filed: Aug. 30, 2000

Related U.S. Application Data

(63) Continuation-in-part of application No. 09/448,130, filed on Nov. 24, 1999.

(51) Int. Cl.$^7$ .................................................. A61M 3/00
(52) U.S. Cl. ...................... 604/43; 604/6.16; 604/524; 138/177
(58) Field of Search ........................ 604/43, 541, 264, 604/266, 270, 523, 528, 524, 4.01, 6.16, 525; 138/118, 172, 177, DIG. 11, 178, 92

(56) References Cited

U.S. PATENT DOCUMENTS

| | | |
|---|---|---|
| 1,879,249 A | 9/1932 | Honsaker |
| 2,116,083 A | 5/1938 | Rusch |
| 3,384,089 A | 5/1968 | Shriner |
| 3,589,368 A | 6/1971 | Jackson et al. |
| 4,037,599 A | 7/1977 | Rauleron |
| 4,134,402 A | 1/1979 | Mahurkar |
| 4,270,542 A | 6/1981 | Plumley |
| 4,311,140 A | 1/1982 | Bridgman |
| 4,368,737 A | 1/1983 | Ash |
| 4,381,011 A | 4/1983 | Somers, 3rd |
| 4,445,897 A | 5/1984 | Ekbladh et al. |
| 4,498,902 A | 2/1985 | Ash et al. |
| 4,529,399 A | 7/1985 | Groshong et al. |
| 4,549,879 A | 10/1985 | Groshong et al. |
| 4,559,039 A | 12/1985 | Ash et al. |
| 4,568,329 A | 2/1986 | Mahurkar |
| 4,583,968 A | 4/1986 | Mahurkar |
| 4,623,327 A | 11/1986 | Mahurkar |
| 4,639,252 A | 1/1987 | Kelly et al. |
| 4,671,796 A | 6/1987 | Groshong et al. |
| 4,692,141 A | 9/1987 | Mahurkar |
| 4,692,153 A | 9/1987 | Berlin et al. |
| 4,701,166 A | 10/1987 | Groshong et al. |
| 4,770,652 A | 9/1988 | Mahurkar |
| 4,772,266 A | 9/1988 | Groshong |
| 4,781,678 A | 11/1988 | de Couët et al. |
| 4,808,155 A | 2/1989 | Mahurkar |
| 4,842,582 A | 6/1989 | Mahurkar |
| 4,895,561 A | 1/1990 | Mahurkar |
| 4,898,669 A | 2/1990 | Tesio |
| 5,053,004 A | 10/1991 | Markel et al. |
| 5,197,951 A | 3/1993 | Mahurkar |
| 5,221,255 A | 6/1993 | Mahurkar et al. |
| 5,221,256 A | 6/1993 | Mahurkar |
| 5,322,519 A | 6/1994 | Ash |
| 5,336,177 A | 8/1994 | Marcus |
| 5,374,245 A | 12/1994 | Mahurkar |
| 5,378,230 A | 1/1995 | Mahurkar |
| 5,451,216 A | 9/1995 | Quinn |
| 5,486,159 A | 1/1996 | Mahurkar |
| 5,571,093 A | 11/1996 | Cruz et al. |
| 5,599,322 A | 2/1997 | Quinn |
| 5,607,405 A | 3/1997 | Decker et al. |
| 5,624,413 A | 4/1997 | Markel et al. |
| 5,685,836 A | 11/1997 | DiPerna et al. |
| 5,776,111 A | 7/1998 | Tesio |
| 5,947,953 A | 9/1999 | Ash et al. |
| 5,984,913 A | 11/1999 | Kritzinger et al. |

FOREIGN PATENT DOCUMENTS

| | | |
|---|---|---|
| GB | 745379 | 2/1956 |

Primary Examiner—Michael J. Hayes
Assistant Examiner—Jeremy Thissell
(74) Attorney, Agent, or Firm—Brinks Hofer Gilson & Lione

(57) ABSTRACT

A hemodialysis catheter including a catheter tube and a bolus tip, the bolus having a radially extending main side port. The catheter also has second and third side ports axially spaced from said main side port. The second and third side ports are each axially elongated, with an edge which is semi-circular in cross-section. The second side port is displaced 180° from the main side port. The third side port is axially aligned with the main port. The catheter is thickened in an arch opposite each of the second and third side ports.

9 Claims, 4 Drawing Sheets

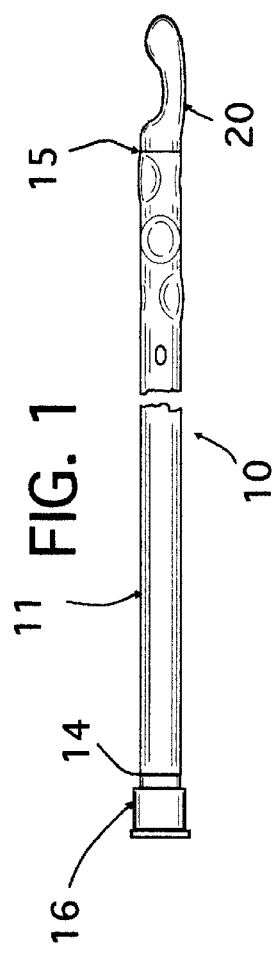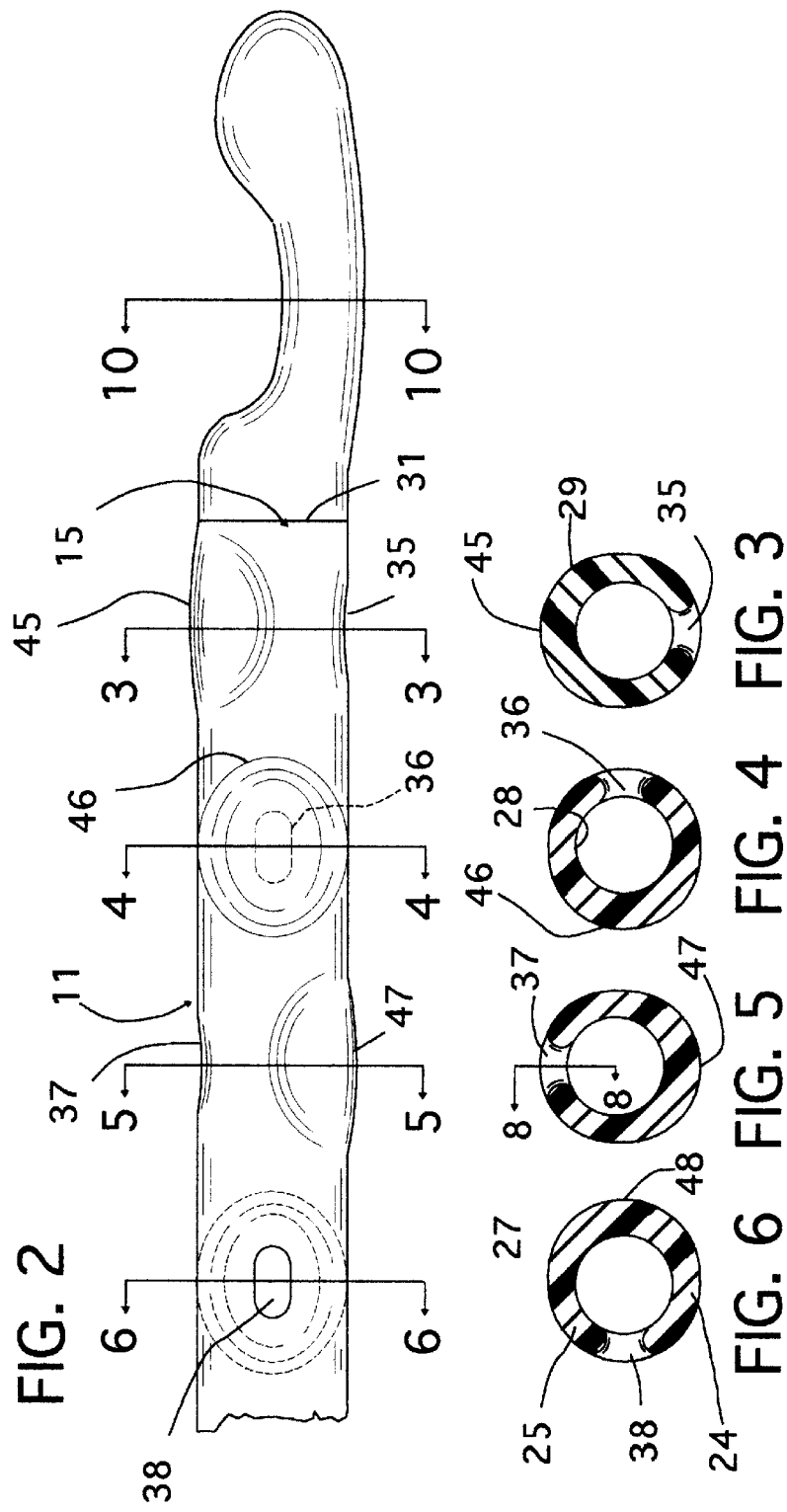

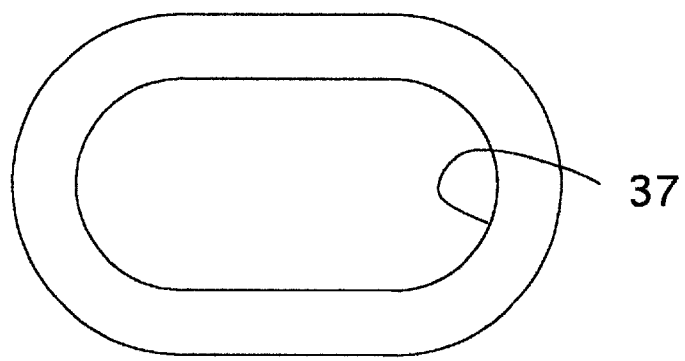
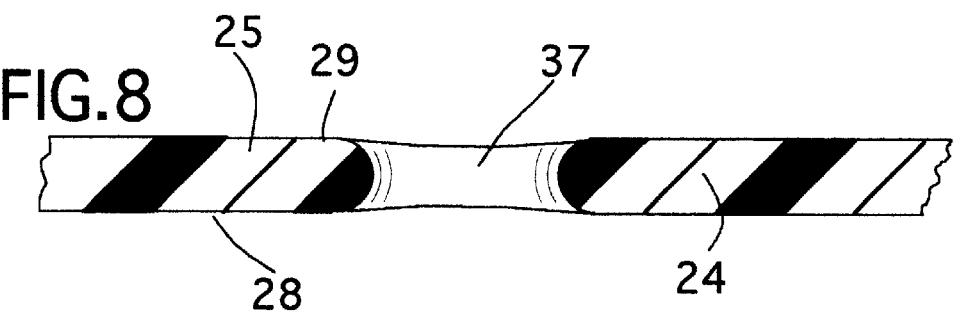
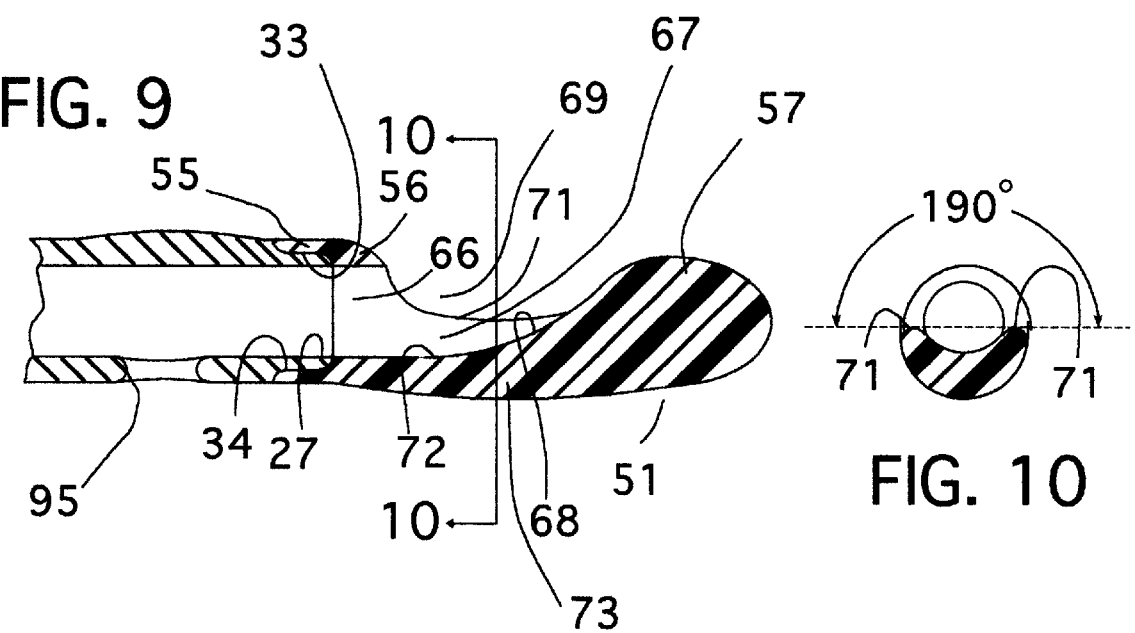

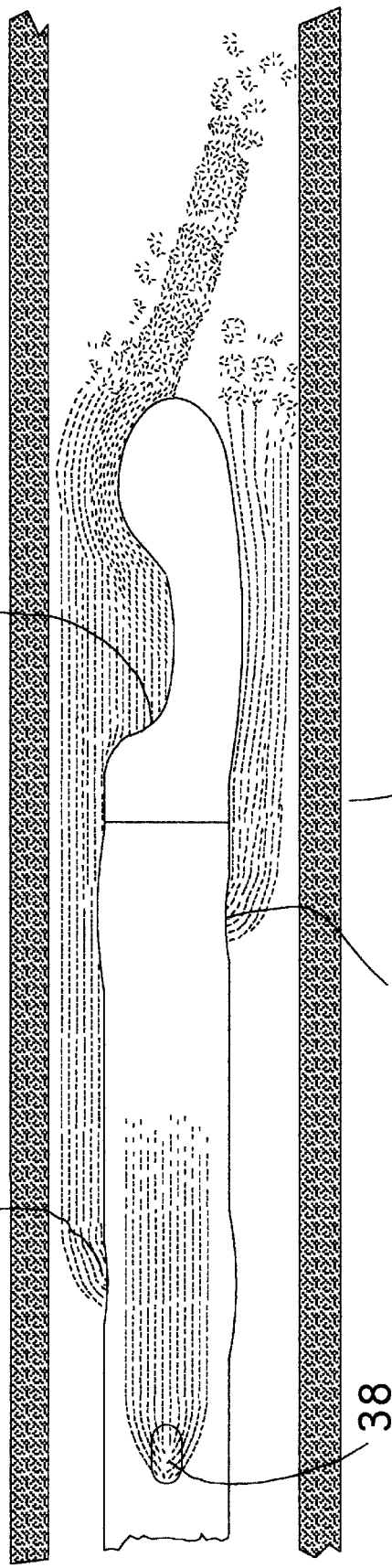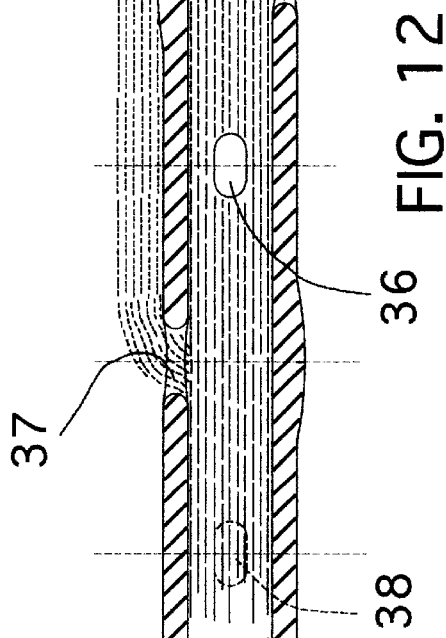

BLOOD VESSEL CATHETER

RELATED APPLICATION

This is a continuation-in-part of application Ser. No. 09/448,130 filed Nov. 24,1999, and entitled HEMODIALYSIS CATHETER.

FIELD OF THE INVENTION

This invention relates in general to medical catheters. It relates, more particularly, to blood vessel catheters.

BACKGROUND OF THE INVENTION

Blood vessel catheters are normally either venous catheters or arterial catheters. Venous catheters, in turn, normally come in several forms. The simplest are short peripheral catheters. Next come midline catheters, central venous catheters and port catheters. Hemodialysis catheters are one form of central venous catheters and are normally placed in the superior vena cava.

The present invention may find application in each of the aforementioned venous catheters. However, it finds particularly advantageous application in hemodialysis catheters.

Hemodialysis, as practiced today, normally employs one of two types of catheter to remove blood from the patient for processing and return processed blood to the patient. Most commonly, a catheter tube containing two lumens is used, each lumen having a semi-cylindrical configuration. This is frequently referred to as a dual lumen catheter. For long-term hemodialysis, surgically implanted vascular access devices are employed. This type of device is described in U.S. Pat. Nos. 4,898,669 and No. 4,108,174.

Flow rates possible with a conventional dual lumen catheter are, as might be expected, lower than those achievable where separate tubular lumens are used to remove blood from a vein for dialysis and then return processed blood back to the vein. Thus, two tube lumens have become more and more popular as the capacity (maximum flow rate) of hemodialysis membranes has increased.

Hemodialysis membranes are now able to process blood at over 500 ml of flow per minute. Even higher processing rates are foreseeable. However, problems occur with both the line introducing purified blood back into the vein (the venous line) and the line removing blood for purification (the arterial or intake line) at flow rates above 300 ml per minute. A high flow rate from the venous line can cause whipping or "firehosing" of the tip in the vein with consequent damage to the vein lining. A corresponding high flow rate into the arterial line causes the port to be sucked into the vein wall, resulting in occlusion. It should be understood, of course, that both lines normally access the superior vena cava and the designations are used for differentiation purposes.

A flow balance between the venous and arterial lines is of obvious importance. Occlusion of the arterial line is a very common limiting factor in hemodialysis. While the venous line tends to remain clear and open, because the direction of flow forces tube ports away from the vein wall, in the arterial line this high flow tends to pull the port against the vein wall, thereby sucking the wall into the port and occluding it. Andersen et al. U.S. Pat. No. 4,594,074, Quinn U.S. Pat. No. 5,451,216, Quinn U.S. Pat. No. 5,810,787, Quinn U.S. Pat. No. 5,599,322 and Quinn U.S. Pat. No. 5,571,093 all discuss the need for improved aspiration in catheters generally.

SUMMARY OF THE INVENTION

An object of the present invention is to provide an improved blood vessel catheter.

Another object is to provide a venous catheter which substantially reduces the opportunity for occlusion to occur.

Another object is to provide an improved hemodialysis catheter which is capable of delivering processed blood to the patient at high flow rates without harmful "firehosing" or whipping of the catheter tip.

A further object is to provide a hemodialysis catheter which is capable of returning processed blood to the patient at flow rates of 500 ml or greater without traumatizing the patients blood vessel.

Yet a further object is to provide a hemodialysis catheter which permits high flow rates while minimizing trauma and potential red cell damage so as to avoid clotting.

Yet another object is to provide a hemodialysis catheter which increases delivered flow rates through the catheter while reducing the force or speed of flow at a bolus end port and at a side port or ports.

Another object is to provide a hemodialysis catheter which permits high flow rates through larger side ports.

The foregoing and other objects are realized in accord with the present invention by providing a venous catheter which combines a radially extending catheter tube and a bolus tip. The bolus tip has a bullet nose and a main side port. A radially extending second side port is displaced 180° around the tube from the main side port and a radially extending third side port is axially aligned with the main side port and 180° displaced from the second side port. The second and third side ports are formed in either the catheter tube, immediately adjacent the bolus, or in an extended bolus passage section. The combination of bolus tip configuration and port configuration and location permits high flow rates with maximum diffusion and minimum occlusion in a venous catheter.

In a first embodiment of the invention, the catheter tube has an elongated cylindrical body, fabricated of resilient plastic. An axial passageway or lumen extends the length of the cylindrical body, from a proximal to a distal end. The cylindrical wall which defines the lumen has an axially and circumferentially spaced series of radially extending ports formed in it adjacent the distal end. Each port is elongated axially of the body so as to have a race-track shaped edge. The race-track shaped edge is, in turn, semi-circular in cross-section around its entire length.

Directly opposite each port in the body of the tube, the body wall is thickened in an oval pattern to form a longitudinally elongated bulge. The bulge forms a stiffening arch in the tube wall. The arch serves to prevent the tube from buckling at the port.

The distal end of the tube has a bolus tip. The bolus tip is a separate element. It is molded of the same resilient plastic. The tip may be glued or welded to the distal end of the tube.

The bolus tip has a tube connector section adjacent the distal end of the tube, a bullet nose section and a passage section between the tube connector section and the bullet nose section. The passage section of the bolus tip has an axial passage in it adjacent the connector section and a radial passage adjacent the nose section. The axial passage is in fluid communication with the tube lumen. The radial passage leads to a main port extending radially through the side of the bolus. The main port extends circumferentially around slightly more than 180° of the bolus, i.e., about 190°.

In a second embodiment of the invention, the passage section of the bolus is extended and the second and third ports are formed in the side of this passage section. This second port is displaced 180° around the axis of the bolus from the main port in the bolus. Directly opposite the second port, the passage section wall is thickened to form a longitudinally elongated bulge. The third port is axially aligned with the main port and 180° displaced from the second port. Directly opposite the third port, the passage section wall is thickened to form a longitudinally elongated bulge.

The bulge opposite the second port stiffens the bolus at the second port and tends to hold the main port away from the vein wall. As such, it aids in preventing occlusion of the main port and, also, protects the vein wall from abrasion by the edge of the main port.

In a conventional hemodialysis catheter, for example, substantially the full pumping force is directed axially out of the end of the catheter because of its end port orientation and the size and shape of any side ports employed. Little flow is directed through such side ports. The present invention provides second and third side ports which allow higher flow rates. This redirection of flow through second and third side ports separated from the main bolus port reduces the speed or force of flow from all three. Fluid pressure is reduced before the fluid reaches the main port. This reduction in force results in better diffusion and protects against whipping." In addition, the port configurations are smoother and have no sharp edges to damage blood cells. During inflow to the catheter, clogging and occlusion due to "vein wall sucking" is substantially avoided.

BRIEF DESCRIPTION OF THE DRAWINGS

The invention, including its construction and method of operation, is illustrated more or less diagrammatically in the drawings, in which:

FIG. 1 is a side elevational view of a first embodiment of hemodialysis catheter comprising features of the present invention;

FIG. 2 is an enlarged side elevational view of the tip end of the catheter of FIG. 1;

FIG. 3 is a sectional view taken along line 3—3 of FIG. 2;

FIG. 4 is a sectional view taken along line 4—4 of FIG. 2;

FIG. 5 is a sectional view taken along line 5—5 of FIG. 2;

FIG. 6 is a sectional view taken along line 6—6 of FIG. 2;

FIG. 7 is an enlarged plan view of one of the catheter tube ports in the catheter embodying features of the invention;

FIG. 8 is a sectional view taken along line 8—8 of FIG. 5;

FIG. 9 is a longitudinal sectional view through the bolus end of the catheter seen in FIGS. 1 and 2;

FIG. 10 is a sectional view taken along line 10—10 of FIG. 2;

FIG. 11 is an enlarged side elevational view of the catheter of FIG. 2 showing the catheter of the invention in position in a patient's blood vessel and the processed blood flow pattern created;

FIG. 12 is a longitudinal sectional view through the catheter seen in FIG. 11;

DESCRIPTION OF THE PREFERRED EMBODIMENTS

Figure 13:
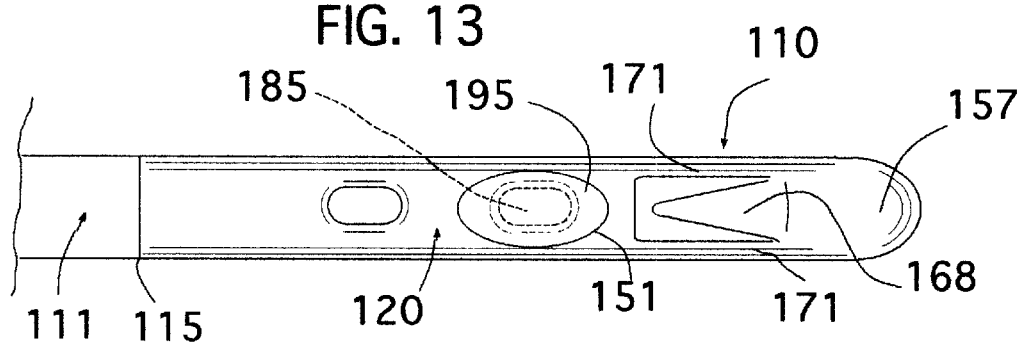
FIG. 13 is a top plan view of a second embodiment of hemodialysis catheter comprising features of the invention, with parts removed.

Referring now to the drawings, and particularly to FIG. 1, a hemodialysis catheter comprising a first embodiment of the invention is seen generally at 10. The catheter 10 includes a cylindrical tube 11 which is preferably fabricated from silicone. Although other plastics, including polyurethane, may be used the properties of silicone have been found to be particularly advantageous for the catheter constructions embodied in the present invention.

The tube 11 extends between a proximal end 14, which may be connected to hemodialysis device, and a distal end 15. As shown in FIG. 1, the proximal end 14 has a conventional connector 16 attached. The tube 11 has a bolus 20 on its distal end 15.

Referring additionally to FIGS. 2–10, the tube 11 comprises a tubular body 24 including a generally cylindrical wall 25 which defines a cylindrical lumen 27 extending through the body, along its entire length. The wall 25 has an inner surface 28 and an outer surface 29.

The distal end 15 of the tube 11 joins the bolus 20 at the line 31. Forward of the line 31 the tube body 24 has a necked down end 33 (see FIG. 9) which is seated in a suitably formed socket 34 in the bolus 20 and glued or ultrasonically welded to the bolus 20.

The tube body 24 has a series of four ports 35, 36, 37 and 38 formed radially through it adjacent the distal end 15 of the tube 11, at longitudinally spaced intervals. The ports 35–38 are, in addition to being longitudinally spaced, also displaced 90° from each other around the circumference of the tube body 24, as best seen in FIGS. 3–6. In compass point terms, the port 35 is at 180°, the port 36 at 90°, the port 37 at 0°/360° and the port 38 at 270°.

The ports 35–38 are identical to each other. Accordingly, only one will be described in detail. The port 37 is formed through the tube body wall 25 during molding so as to have a race-track shape longitudinally of the tube 11. In a standard 10 French tube, the port 37 is 0.100 inches long and 0.050 inches wide.

As seen in FIGS. 5 and 8, the edge 39 of the race-track shaped port is semi-circular in cross-section, i.e., rounded along its entire length. In a 10 French tube, the wall 25 is 0.030 inches thick where the port 37 is formed, so the radius of the semi-circle is 0.015 inches. It should be understood, of course, that if tube wall 25 thickness changes because different size tubes are employed, the radius will change accordingly.

In the tube 11 illustrated, the ports 35–38 are spaced longitudinally so that their centerlines, seen as the section lines 3, 4, 5 and 6 in FIG. 2, are 0.175 inches apart. The centerline of the port 35, in turn, is spaced 0.175 inches from the approximate centerline of the main bolus port which is hereinafter described.

Directly opposite each of the ports 35–38 in the tube wall 25, the wall is thickened in an oval pattern to form an elongated bulge. At its thickest, each bulge 45, 46, 47 and 48 is about 40% thicker than the rest of the tube wall 25. The bulge, best seen in FIG. 2, is centered on the corresponding port opposite it. Thus, what amounts to an oval shaped stiffening arch is formed in the tube wall 25 opposite each port, the arch being about two and one-half times as long as the corresponding port; stiffening arches 45, 46, 47 and 48 being opposite ports 35, 36, 37 and 38, respectively. The arches 45, 46, 47 and 48 stiffen the tube 11 where it otherwise might buckle because a port (35–38) opposite it has been elongated longitudinally to increase its flow capacity.

Referring specifically to FIG. 9, the bolus 20 and its connection to the terminal end 15 of the catheter tube 11 are shown in greater detail. The bolus 20 has a generally bullet-shaped body 51 fabricated from silicone. The dimensions of the body 51 vary with the size of the catheter tube 11 in use, but its outside diameter substantially equals that of the tube.

The body 51 of the bolus 20 is formed by injection molding and has an overall length of 0.510 inches, as made for the 10 French tube. The bolus body 51 comprises three distinct body sections; a tube connector section 55, a flow passage section 56 and a nose section 57.

The necked down end 33 of the tube body 24 is seated in the socket 34 formed in the section 55 of the bolus body 51. The end 33 is glued or welded in the socket 34. The bolus body 51 and the remainder of the tube body 24 have substantially the same outside diameter, as has been pointed out.

The lumen 27 in the tube body 24 communicates with the flow passage section 56 in the bolus body 51. The passage section 56 contains a short, axially extending passage 66 and a longer axially and radially extending passage 67 having a base 68 which curves across the axis of the body 51 to form one end of a main port 69 opening through the side of the bolus body. The main port 69 is enlarged by forming low sides 71 for the passage 67 so that the main port 69 extends circumferentially around about 190° of the body 51, as seen in FIG. 10.

Directly opposite the center of the main port 69, the floor 72 of the radial passage 67 is thickened, as at 73, to form a stiffening arch in the bolus 20. The arch 73 begins at about the end of the tube body 24, increases in thickness until it is directly under the main port 69, and then decreases in thickness to the front end of the nose section 57.

Referring now to FIG. 11, the catheter 10 embodying features of a first form of the invention is shown in place in a patient's vein V, in use as a hemodialysis catheter with processed blood being delivered through it into the vein. Processed blood flowing through the lumen 27 under pressure exits through each of the four ports 35–38 in the lumen and through the bolus main port 69. FIG. 12 shows the same catheter 10 in longitudinal section (without the blood vessel) to better illustrate flow through each port 35–38 and 69.

As will be seen, the lumen second port 35, which is immediately adjacent the bolus 20, is displaced 180° around the axis of the lumen 27 and bolus 20 from the bolus main port 69. As a result, the reaction forces created by the exiting processed blood and acting on the catheter 10 at its bolus end are substantially balanced.

Rearwardly of the port 35, processed blood is forced out of the third, fourth and fifth ports 36, 37 and 38 at 90° displaced locations around the axis of the tube 11. As a result, processed blood is returned to the patient from five ports at a high rate of flow, but with reaction forces which also tend to be balanced along the tube 11 so as to avoid whipping of any part of the tube in the blood vessel. Flow rates of 500 m/min. are achievable with little or no vessel trauma.

At the same time that forces exerted by processed blood flow are balanced by the afore-described port arrangement, the configuration of the ports 35–38 contributes greatly to smooth flow and minimal blood corpuscle damage. Because the ports 35–38 are longitudinally elongated and have rounded edges, the processed blood under pressure flows smoothly out of them and tends to adhere to the outer surface 29 of the tube body 24 as it flows toward and over the bolus 20.

Figure 14:
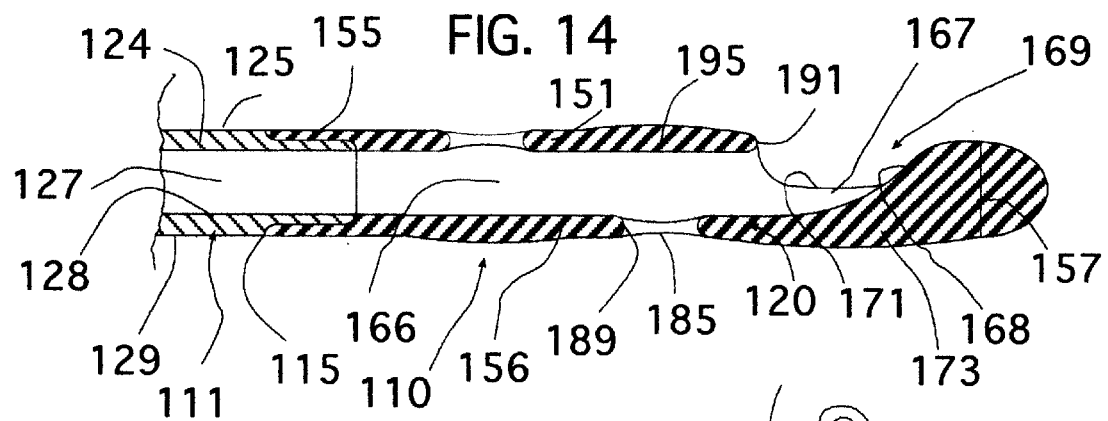
FIG. 14 is a sectional view taken along line 14—14 of FIG. 13.
Figure 15:
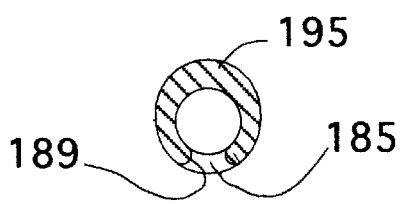
FIG. 15 is a sectional view taken along line 15—15 of FIG. 13.

Referring now to FIGS. 13–15, a catheter comprising features of a second embodiment of the invention is generally at 110. The catheter 110 includes a cylindrical tube 111 preferably fabricated of silicone. The proximal end of the tube 111 has a connector (not shown) attached in a conventional manner. The distal end 115 of the tube 111 has a bolus 120 mounted thereon.

The tube 111 in the catheter 110 comprises a tubular body 124, including a generally cylindrical wall 125 which defines a cylindrical lumen 127 extending through the body, along its entire length. The wall 125 has an inner surface 128 and an outer surface 129.

The bolus 120 in the catheter 110 has a body 151. The body 151 comprises a connector section 155, an elongated flow passage section 156 and a bullet-nose section 157.

The lumen 127 in the tube body 124 communicates with the flow passage section 156 in the bolus body 151. The flow passage section 156 in the body 151 includes an elongated, axially extending passage 166 and a shorter, axially and radially extending passage 167 having a base 168 which curves across the axis of the body 151 to form one end of a main port 169 in the side of the bolus body. The main port 169 is enlarged by forming low sides 171 for the radial passage 167 so that the main port extends circumferentially around about 190° of the body 151.

Directly opposite the center of the main port 169 the floor 172 of the radial passage 167 is thickened, as at 173, to form a stiffening arch in the bolus 120. The arch 173 begins under the elongated, axially extending passage 166, increases in thickness until it is directly under the port 169, and then decreases in thickness toward the front end of the nose section 157.

The elongated flow passage section 156 of the bolus body 151 also has a second port 185 formed radially through it. The port 185 is circumferentially displaced 180° from the main port 169 around the longitudinal axis of the bolus 120.

The port 185 is formed during molding so as to have a race-track shape longitudinally of the section 156. In a standard 10 French hemodialysis tube assembly, the port 185 is 0.100 inches long and 0.050 inches wide.

As seen in FIG. 14 the edge 189 of the race-track shaped port 185 is semi-circular in cross-section. In other words, it is rounded along its entire length.

Directly opposite the second port 185, the wall of the passage section 156 is thickened in an oval pattern to form an elongated bulge 195. At its thickest, the bulge 195 is about 40% thicker than the rest of the wall. The bulge 195 amounts to an oval shaped stiffening arch formed in the wall of the passage section 156 opposite the second port 185, the arch being about two and one-half times as long as the port.

The arch formed by the bulge 195 serves multiple purposes in the catheter 110. It prevents the bolus 120 from buckling at the second port 185. It stiffens the edge 191 of the main port 169 where it emerges from the bolus body 151. It serves to hold the main port 169 away from the vein wall and protect the vein wall from abrasion by the edge 191 of the main port.

The elongated flow passage section 156 of the bolus body 151 also has a third port 198 formed radially through it. The port 198 is circumferentially displaced 180° from the second port 185 around the longitudinal axis of the bolus 120. In other words, it is axially aligned with the main port 169.

The port 198 is also formed during molding so as to have a race-track shape longitudinally of the section 156. The port 198 is 0.100 inches long and 0.050 inches wide.

The edge 199 of the race-track shaped port 198 is semi-circular in cross-section. In other words, it is rounded along its entire length.

Directly opposite the third port 198, the wall of the passage section 156 is thickened in an oval pattern to form an elongated bulge 205. Again, the bulge 205 amounts to an oval shaped stiffening arch formed in the wall of the passage section 156 opposite the section port 198, the arch being about two-and-one-half times as long as the port.

The arch formed by the bulge 205 serves multiple purposes in the catheter 110. It prevents the bolus 120 from buckling at the third port 198. It serves to hold the second port 185 away from the vein wall and protect the vein wall from abrasion by the edge 191 of the main port.

Figure 16:
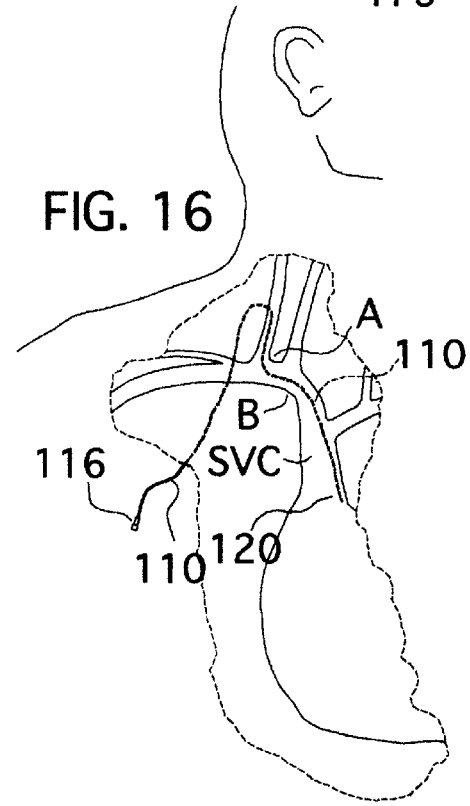
FIG. 16 is an illustration of portions of a patient's anatomy, showing placement of a catheter embodying features of the invention in the patient's superior vena cava.

Referring now to FIG. 16, a catheter 110 embodying features of the invention is shown there in place in the superior vena cava (SVC) of a patient. The catheter 110 has been introduced through the external jugular vein in the patient's neck and fed through that vein into the SVC.

As will be seen, in following this course the catheter bolus 20 has to lead the catheter around what amounts to two 90° bends to get to the SVC. The bends are indicated at A and B. In navigating the bends, the bullet-nosed body 151 of the bolus 120 tends to slide along the surface of the vein wall, without abrading the wall as it passes. As a result, vein wall damage is avoided during insertion; such damage being a common occurrence with conventional catheters.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A catheter for insertion into a patient's blood vessel comprising:
   a) an elongated tube including a body having a proximal end and a distal end;
   b) said body including a cylindrical wall having an inner surface and an outer surface;
   c) a lumen inside said inner surface of said wall, said lumen extending through said body from said proximal end to said distal end;
   d) a longitudinally elongated bolus on said distal end of said body, said bolus having a nose section and a passage section, said passage section containing a passage extending to a main port in the side of said passage section;
   e) a radially extending second port in one of said tube body wall and said bolus passage section;
   f) said second port being angularly displaced around said catheter from said main port; and
   g) a bulge formed opposite said second port in one of said tube body wall and said passage section;
   h) said bulge comprising a stiffening arch.

2. The catheter of claim 1 further characterized in that:
   a) said second port is displaced approximately 180° around said catheter from said main port.

3. The catheter of claim 1 further characterized by and including:
   a) a radially extending third port in one of said tube body wall and said passage section;
   b) a bulge formed opposite said third port in one of said tube body wall and said passage section;
   c) said bulge comprising a stiffening arch.

4. The catheter of claim 3 further characterized in that:
   a) at least said second port is longitudinally elongated so as to have a racetrack configuration.

5. The catheter of claim 3 further characterized in that:
   a) said second and third ports each have a semi-circular side edge extending entirely around the port.

6. The catheter of claim 3 further characterized in that:
   a) said third port is approximately axially aligned with said main port and displaced approximately 180° around said catheter from said second port.

7. A catheter for insertion into a patient's blood vessel, comprising:
   a) an elongated tube including a body having a proximal end and a distal end;
   b) said body including a generally cylindrical wall having an inner surface and an outer surface;
   c) a lumen inside said inner surface of said wall, said lumen extending through said body from said proximal end to said distal end;
   d) a radially extending port in said tube body wall; and
   e) a bulge formed opposite said port in said tube body wall;
   g) said bulge comprising a stiffening arch in said tube.

8. The catheter of claim 7 further characterized in that:
   a) said tube body is formed of a silicone plastic.

9. The catheter of claim 7 further characterized in that:
   a) said tube body is formed of a polyurethane plastic.

* * * * *